(12) United States Patent
Ahn et al.

(10) Patent No.: US 8,811,610 B2
(45) Date of Patent: Aug. 19, 2014

(54) METHOD, MEDIUM, AND SYSTEM FOR ENCRYPTING AND/OR DECRYPTING INFORMATION OF MICROARRAY

(75) Inventors: Taejin Ahn, Seoul (KR); Kyunghee Park, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 641 days.

(21) Appl. No.: 12/232,398

(22) Filed: Sep. 17, 2008

(65) Prior Publication Data

US 2009/0252322 A1 Oct. 8, 2009

(30) Foreign Application Priority Data

Dec. 24, 2007 (KR) .................. 10-2007-0136398

(51) Int. Cl.
*H04L 9/00* (2006.01)
(52) U.S. Cl.
USPC .................................................... 380/44
(58) Field of Classification Search
USPC .................................................... 380/44
See application file for complete search history.

(56) References Cited

U.S. PATENT DOCUMENTS

| 6,901,145 | B1 * | 5/2005 | Bohannon et al. | 380/44 |
| 2002/0129251 | A1 * | 9/2002 | Itakura et al. | 713/176 |
| 2004/0101191 | A1 * | 5/2004 | Seul et al. | 382/151 |
| 2004/0163412 | A1 * | 8/2004 | Olek | 63/3 |
| 2004/0185481 | A1 | 9/2004 | Numajiri | |
| 2005/0053968 | A1 * | 3/2005 | Bharadwaj et al. | 435/6 |
| 2006/0222227 | A1 * | 10/2006 | Seul et al. | 382/128 |
| 2009/0110192 | A1 * | 4/2009 | Elrod et al. | 380/44 |

FOREIGN PATENT DOCUMENTS

| JP | 2006277541 A | 10/2006 |
| KR | 1020050051221 A | 11/2003 |
| KR | 1020050083594 A | 8/2005 |

OTHER PUBLICATIONS

Federal Information Processing Standards Publication 197, Announcing the Advanced Encryption Standard (AES) Nov. 26, 2001.

* cited by examiner

*Primary Examiner* — William Powers
*Assistant Examiner* — Stephen Sanders
(74) *Attorney, Agent, or Firm* — Leydig, Voit & Mayer, Ltd.

(57) ABSTRACT

Provided is a method of encrypting information of a microarray. The method includes: acquiring genetic information of a person by scanning the microarray; generating a secret key for identifying the unique property of the person from the acquired genetic information; and encrypting the acquired genetic information by using the generated secret key. Accordingly, the method can prevent the leakage of the genetic information of the person and protect the person's privacy.

17 Claims, 11 Drawing Sheets
(2 of 11 Drawing Sheet(s) Filed in Color)

FIG. 2A

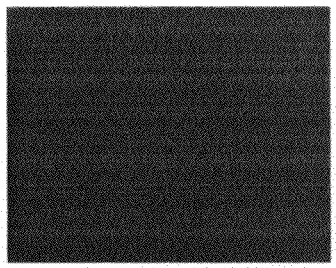

| no | rs | no | rs | no | rs |
|---|---|---|---|---|---|
| SNP1 | rs1024116 | SNP27 | rs2663 | SNP53 | rs5000563 |
| SNP2 | rs1028484 | SNP28 | rs2735096 | SNP54 | rs6906846 |
| SNP3 | rs10456057 | SNP29 | rs2844615 | SNP55 | rs6928954 |
| SNP4 | rs1051336 | SNP30 | rs28481932 | SNP56 | rs7194 |
| SNP5 | rs1335873 | SNP31 | rs2856816 | SNP57 | rs732889 |
| SNP6 | rs1431403 | SNP32 | rs2975046 | SNP58 | rs734701 |
| SNP7 | rs1632879 | SNP33 | rs3094674 | SNP59 | rs7382297 |
| SNP8 | rs1632882 | SNP34 | rs3115637 | SNP60 | rs772436 |
| SNP9 | rs1632883 | SNP35 | rs3117229 | SNP61 | rs7756262 |
| SNP10 | rs1655900 | SNP36 | rs3128963 | SNP62 | rs7761068 |
| SNP11 | rs1655904 | SNP37 | rs3128965 | SNP63 | rs7763822 |
| SNP12 | rs1655906 | SNP38 | rs3128966 | SNP64 | rs7764491 |
| SNP13 | rs1979255 | SNP39 | rs3129872 | SNP65 | rs8037429 |
| SNP14 | rs2027852 | SNP40 | rs3129877 | SNP66 | rs873289 |
| SNP15 | rs2068204 | SNP41 | rs3130693 | SNP67 | rs9268645 |
| SNP16 | rs2179920 | SNP42 | rs3132486 | SNP68 | rs9272219 |
| SNP17 | rs2248880 | SNP43 | rs3135021 | SNP69 | rs9272346 |
| SNP18 | rs2295120 | SNP44 | rs3135392 | SNP70 | rs9272723 |
| SNP19 | rs2508037 | SNP45 | rs3135393 | SNP71 | rs9277542 |
| SNP20 | rs2517716 | SNP46 | rs3177928 | SNP72 | rs9295984 |
| SNP21 | rs2517719 | SNP47 | rs3243 | SNP73 | rs9296073 |
| SNP22 | rs2523544 | SNP48 | rs354439 | SNP74 | rs9348904 |
| SNP23 | rs2523575 | SNP49 | rs417162 | SNP75 | rs9368669 |
| SNP24 | rs2524067 | SNP50 | rs4394275 | SNP76 | rs9378249 |
| SNP25 | rs2524078 | SNP51 | rs439935 | SNP77 | rs9405035 |
| SNP26 | rs2596477 | SNP52 | rs4988822 | SNP78 | rs959566 |

FIG. 4

| SAMPLE ID | PID |
|---|---|
| GSM116887 | AAAABBBBABBBAAABBBABBBABAAAABBBBAAABBBBBABBBAAAAAABB<br>BBAAABBBAAABBBABBBBBABAAAABBBBABBBBBBBAAAAAAABABABAB<br>ABAABBABAAAAAAABABAAABAAABBBABBBBBBBBBAAABBBBBBBAABB |
| GSM116888 | AAAABBABABBBAAAAABABBBAAABABBBBBAABBBBBBAABBAAABAAAB<br>BBAABBBBAAAABBBBABBBAAABAAABBBBBBBBBABAAAAAABBABABAB<br>BBAABBABAAABAAABABAAABAAAAABABABBBAAABAAABBBABBBAABB |
| GSM116889 | ABAAABAAABBBAAABABABBBABABBBABABAAABBBBBABBBAABBAAAB<br>ABAABBBBAAABBBBBABBBAABBAAAABBBBBBBBAAAAAAAAABABABAA<br>ABABBBAAAABBAAABAAAAABABAAAABBABBBBBAAAAABBBABABAABB |
| GSM116890 | AAAAAAABBBBBABABBBBBBBABAABBAABBABABBBABABABABAABBAABB<br>AAAAABABAAAABBBBBBABAABBABABBBABBBABAAABAAABAAAAABAA<br>BBAABBBBABABABABAAAAAAAAAABBABBBABAAABBBABABABAAAB |
| GSM116891 | AAAABBAABBBBABBBBBBBBAAAAABBBBAAABBBBBABABABABAAAABB<br>BBAABBBBABABBBBBBABABBBABBBBBBBBBBBBAABBABAAAAABAA<br>BBBBABAABBBBAABBAAABAAAAAABBBBABBBAABBABBBABABBBABBB |
| GSM116892 | ABAABBAAABBBABABABABBBAAABABBBABAAAABBABABABABABAAAB<br>BBAABBBBABAABBBBABABAABBABABBBBBBBBBABAAABABABABABAA<br>BBABBBABABBBABBBAAAAABABAAABBBABBBBBABABABABABABABBB |

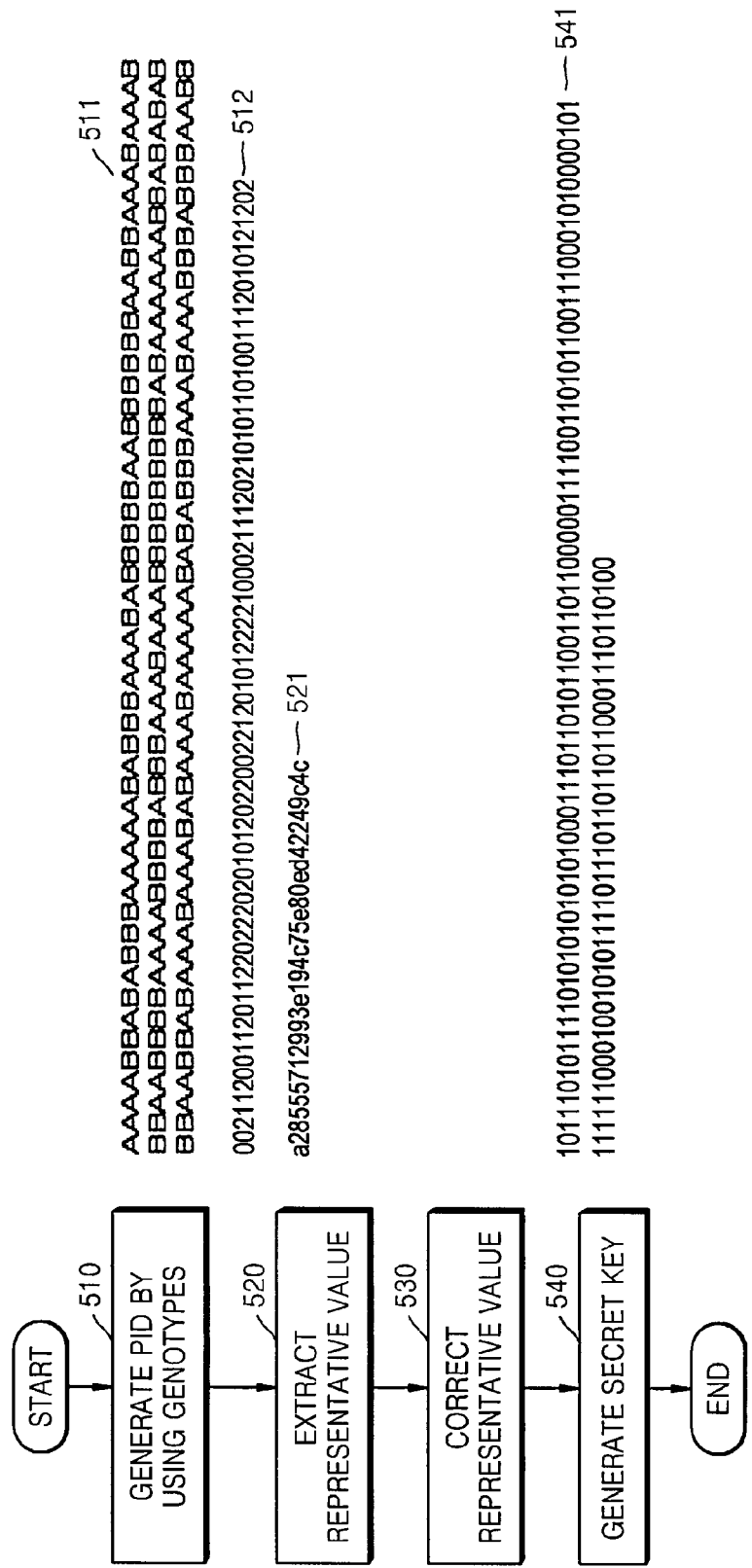

```
00000000h: FF D8 FF E0 00 10 4A 46 49 46 00 01 01 01 00 60
00000010h: 00 60 00 00 FF DB 00 43 00 08 06 06 07 06 05 08
00000020h: 07 07 07 09 09 08 0A 0C 14 0D 0C 0B 0B 0C 19 12
00000030h: 13 0F 14 1D 1A 1F 1E 1D 1A 1C 1C 20 24 2E 27 20
00000040h: 22 2C 23 1C 1C 28 37 29 2C 30 31 34 34 34 1F 27
00000050h: 39 3D 38 32 3C 2E 33 34 32 FF DB 00 43 01 09 09
00000060h: 09 0C 0B 0C 18 0D 0D 18 32 21 1C 21 32 32 32 32
00000070h: 32 32 32 32 32 32 32 32 32 32 32 32 32 32 32 32
00000080h: 32 32 32 32 32 32 32 32 32 32 32 32 32 32 32 32
00000090h: 32 32 32 32 32 32 32 32 32 32 32 32 32 32 FF C0
000000a0h: 00 11 08 0A 00 0A 00 03 01 22 00 02 11 01 03 11
000000b0h: 01 FF C4 00 1F 00 00 01 05 01 01 01 01 01 01 00
000000c0h: 00 00 00 00 00 00 00 01 02 03 04 05 06 07 08 09
000000d0h: 0A 0B FF C4 00 B5 10 00 02 01 03 03 02 04 03 05
000000e0h: 05 04 04 00 00 01 7D 01 02 03 00 04 11 05 12 21
000000f0h: 31 41 06 13 51 61 07 22 71 14 32 81 91 A1 08 23
00000100h: 42 B1 C1 15 52 D1 F0 24 33 62 72 82 09 0A 16 17
00000110h: 18 19 1A 25 26 27 28 29 2A 34 35 36 37 38 39 3A
00000120h: 43 44 45 46 47 48 49 4A 53 54 55 56 57 58 59 5A
00000130h: 63 64 65 66 67 68 69 6A 73 74 75 76 77 78 79 7A
00000140h: 83 84 85 86 87 88 89 8A 92 93 94 95 96 97 98 99
00000150h: 9A A2 A3 A4 A5 A6 A7 A8 A9 AA B2 B3 B4 B5 B6 B7
00000160h: B8 B9 BA C2 C3 C4 C5 C6 C7 C8 C9 CA D2 D3 D4 D5
00000170h: D6 D7 D8 D9 DA E1 E2 E3 E4 E5 E6 E7 E8 E9 EA F1
00000180h: F2 F3 F4 F5 F6 F7 F8 F9 FA FF C4 00 1F 01 00 03
00000190h: 01 01 01 01 01 01 01 01 01 00 00 00 00 00 00 01
000001a0h: 02 03 04 05 06 07 08 09 0A 0B FF C4 00 B5 11 00
```

METHOD, MEDIUM, AND SYSTEM FOR ENCRYPTING AND/OR DECRYPTING INFORMATION OF MICROARRAY

CROSS-REFERENCE TO RELATED PATENT APPLICATION

This application claims the benefit of Korean Patent Application No. 10-2007-0136398, filed on Dec. 24, 2007, in the Korean Intellectual Property Office, the disclosure of which is incorporated herein in its entirety by reference.

BACKGROUND

1. Field

One or more embodiments of the present invention relate to a method, medium, and system for encrypting and/or decrypting information of a microarray, and more particularly, to a method, medium, and system for encrypting and/or decrypting information of a deoxyribonucleic acid (DNA) microarray.

2. Description of the Related Art

Microarrays are divided into a deoxyribonucleic acid (DNA) chip, a protein chip, a cell chip, a neuron chip, etc., according to materials attached to a surface. DNA microarrays refer to a high-density array of DNA molecules with known base sequences on a small substrate. In detail, DNA microarrays refer to a microarray of probes immobilized at predefined positions on a solid surface, e.g., a glass slide, nylon, silicon, or silica.

When a target DNA fragment to be analyzed is combined to a DNA microarray, probes affixed to the DNA microarray and base sequences of the target DNA fragment are hybridized depending on the level of complementarity. It is possible to analyze the base sequences of the target DNA fragment by detecting and understanding the hybridization by an optical or radioactive chemical method (sequencing by hybridization).

Since a DNA microarray contains tens of thousands of gene fragments, information of genes can be obtained through one test. In other words, unlike conventional technology focusing on some genes, DNA microarray technology can obtain lots of information at once.

SUMMARY

One or more embodiments of the present invention provide a method and system for encrypting information of a microarray which can prevent the leakage of individual genetic information, and a computer-readable medium having a computer readable code to implement the method.

One or more embodiments of the present invention also provide a method and system for decrypting encrypted information of a microarray which can prevent the leakage of individual genetic information, and a computer-readable medium having a computer readable code to implement the method.

Additional aspects and/or advantages will be set forth in part in the description which follows and, in part, will be apparent from the description, or may be learned by practice of the invention.

According to an aspect of the present invention, there is provided a method of encrypting information of a microarray, the method comprising: acquiring genetic information of a person by scanning the microarray; generating a secret key for identifying the unique property of the person from the acquired genetic information; and encrypting the acquired genetic information by using the generated secret key.

According to another aspect of the present invention, there is provided a computer-readable medium having a computer readable code to implement a method of encrypting information of a microarray, the method comprising: acquiring genetic information of a person by scanning the microarray; generating a secret key for identifying the unique property of the person from the acquired genetic information; and encrypting the acquired genetic information by using the generated secret key.

According to another aspect of the present invention, there is provided a method of decrypting information of a microarray, the method comprising: acquiring encrypted data corresponding to the information of the microarray; acquiring a secret key for identifying the unique property of a person from genetic information of the person; and decrypting the encrypted data by using the acquired secret key.

According to another aspect of the present invention, there is provided a computer-readable medium having a computer readable code to implement a method of decrypting information of a microarray, the method comprising: acquiring encrypted data corresponding to the information of the microarray; acquiring a secret key for identifying the unique property of a person from genetic information of the person; and decrypting the encrypted data by using the acquired secret key.

According to another aspect of the present invention, there is provided a system for encrypting information of a microarray, the system comprising: a genetic information acquiring unit to acquire genetic information of a person by scanning the microarray; a secret key generating unit to generate a secret key for identifying the unique property of the person from the acquired genetic information; and an encrypting unit to encrypt the acquired genetic information by using the generated secret key.

According to another aspect of the present invention, there is provided a system for decrypting information of a microarray, the system comprising: a data acquiring unit to acquire encrypted data corresponding to the information of the microarray; a secret key acquiring unit to acquire a secret key for identifying the unique property of a person from genetic information of the person; and a decrypting unit to decrypt the encrypted data by using the acquired secret key.

BRIEF DESCRIPTION OF THE DRAWINGS

The patent or application file contains at least one drawing executed in color. Copies of this patent or patent application publication with color drawings will be provided by the office upon request and payment of the necessary fee.

These and/or other aspects and advantages will become apparent and more readily appreciated from the following description of the embodiments, taken in conjunction with the accompanying drawings of which:

FIG. 2A illustrates image data output from a genetic information acquiring unit included in the system of FIG. 1 according to an embodiment of the present invention;

FIG. 2B illustrates numerical data output from the genetic information acquiring unit included in the system of FIG. 1 according to an embodiment of the present invention;

FIG. 3 illustrates markers used to generate a personal identification (PID) in a secret key generating unit included in the system of FIG. 1 according to an embodiment of the present invention;

FIG. 4 illustrates PIDs generated in the secret key generating unit included in the system of FIG. 1 according to an embodiment of the present invention;

FIG. 5 is a flowchart illustrating the operation of the secret key generating unit included in the system of FIG. 1 according to an embodiment of the present invention;

DETAILED DESCRIPTION OF THE EMBODIMENTS

Figure 1:
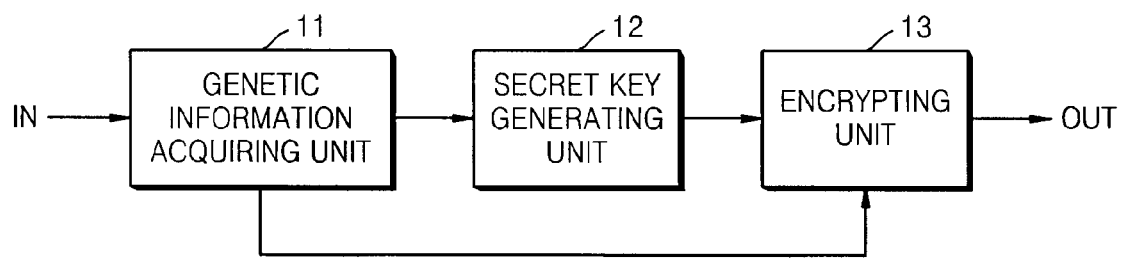
FIG. 1 is a block diagram of a system for encrypting information of a microarray according to an embodiment of the present invention.

Reference will now be made in detail to embodiments, examples of which are illustrated in the accompanying drawings, wherein like reference numerals refer to the like elements throughout. In this regard, embodiments of the present invention may be embodied in many different forms and should not be construed as being limited to embodiments set forth herein. Accordingly, embodiments are merely described below, by referring to the figures, to explain aspects of the present invention.

FIG. 1 is a block diagram of a system for encrypting information of a microarray according to an embodiment of the present invention.

Referring to FIG. 1, the system may include a genetic information acquiring unit 11, a secret key generating unit 12, and an encrypting unit 13.

The genetic information acquiring unit 11 may acquire genetic information by scanning the microarray. In detail, the genetic information acquiring unit 11 may acquire image data by scanning the microarray and acquire numerical data from the image data. For example, the genetic information acquiring unit 11 may be a scanner. The scanner may be an optical scanner, an electro scanner, or an electromagnetic scanner.

FIG. 2A illustrates image data output from the genetic information acquiring unit 11 included in the system of FIG. 1 according to an embodiment of the present invention. FIG. 2B illustrates numerical data output from the genetic information acquiring unit 11 included in the system of FIG. 1.

Referring to FIGS. 2A and 2B, the image data of FIG. 2A represents genetic information of a person. Accordingly, when the image data is transmitted to a computer through a communication network, such as the Internet, in the form of a plaintext (that is, an un-encrypted) image file, the genetic information may be leaked without consent of the person, thereby invading the person's privacy.

The numerical data of FIG. 2B is data generated from the image data of FIG. 2A, and also represents the genetic information of the person. Accordingly, like the image data, when the numerical data is transmitted in the form of a plaintext numeric file, the genetic information of the person may be leaked.

Referring to FIG. 1 again, the secret key generating unit 12 may generate a secret key for identifying the unique property of the person from the genetic information acquired by the genetic information acquiring unit 11. In detail, the secret key generating unit 12 may generate a personal identification (PID) from genotypes of one or more markers of the acquired genetic information and generates a secret key from the generated PID.

Here, the secret key is an encryption key shared by only a sender and a receiver of a message in a symmetric key or secret key cryptography. The secret key cryptography is a method in which both the sender and the receiver use the same key to encrypt and decrypt data. In detail, the secret key cryptography is a method of transmitting encrypted data from the sender to the receiver in such a way that nobody other than the receiver can receive and decrypt the data by using the secret key.

Here, the markers are used to identify the unique property of the person among the genetic information acquired from the microarray. In detail, most of a plurality of pieces of genetic information acquired from the microarray are the same irrespective of samples, but some of the plurality of pieces of genetic information acquired from the microarray may be different according to the samples. Accordingly, the samples can be distinguished from one another by using the some of the plurality of pieces of genetic information as markers, thereby making it possible to identify the unique property of the person. There may be many methods of selecting markers. A method of selecting markers will now be explained.

First, markers included in the microarray among markers showing polymorphism, which has been used to identify genes, may be used. Polymorphism refers to the occurrence of two or more forms or alleles within the same species. In other words, forms or alleles varying depending on samples can be predicted by using markers showing polymorphism, which will be explained later with reference to FIG. 3.

Second, data mining may be used for some or all of the data of the microarray. Data mining is a process of sorting through a huge volume of data and systemically and automatically discovering statistical rules or patterns. In detail, data mining is a process of analyzing data to unearth previously unrecognized relationships between data. Accordingly, markers may be selected by analyzing relationships between some or all of the data of the microarray.

FIG. 3 illustrates markers used to generate a PID in the secret key generating unit 12 included in the system of FIG. 1 according to an embodiment of the present invention. A method of selecting markers will now be explained in detail with reference to FIGS. 1 and 3.

Referring to FIG. 3, 'no' denotes 78 single nucleotide polymorphisms (SNPs), and 'rs(reference SNP)' denotes genotypes respectively corresponding to the SNPs.

SNP refers to one or tens of base variations among 3 billion base sequences of a chromosome in a cell nucleus from different individuals. When hundreds of DNA base sequences of many people are compared and read, different bases are present in a single position which is called SNP. SNP occurs at a frequency of one SNP about every 1000 bases.

Since a human being has approximately 0.3 million base pairs, he/she has at least 1 million variations. Human beings are 99.9% identical at the gene sequence level. The 0.1% variations in SNP, however, produce differences in height, skin color, etc. Most SNPs are used as markers indicating genetic proximity. Accordingly, SNP patterns can be analyzed to identify genetic susceptibility to a disease and genetic causes of a disease, and help design better drugs.

Predetermined markers may be selected from among markers showing conventionally studied polymorphism, e.g., SNPs. The markers showing the polymorphism may include markers used in various theses and markers suggested by the National Institute of Health (NIH).

In this case, the number of markers may be adjusted according to the number of samples. As the number of markers decreases, the number of identifiable samples decreases. As the number of markers increases, the number of identifiable samples increases. In other words, when there are a lot of samples, the number of markers may be increased. In detail, the number of samples may be the number of probes analyzable from the microarray.

FIG. 4 illustrates PIDs generated in the secret key generating unit 12 included in the system of FIG. 1. The operation of the secret key generating unit 12 will now be explained with reference to FIGS. 1 and 4.

Referring to FIG. 4, 'SAMPLE ID' denotes sample identifications and 'PID(Personal Identification)' denotes PIDs respectively according to samples.

The secret key generating unit 12 can generate a PID by combining genotypes of SNPs. A genotype is a set of genes possessed by an individual organism. Since a genotype in one SNP is expressed with two letters, genotypes corresponding to one SNP may be represented as AA, BB, and AB. Accordingly, when 78 SNPs are used as markers, $3^{78}(+1.64e37)$ samples can be distinguished.

In further detail, the secret key generating unit 12 may generate a PID by sequentially combining the 78 SNPs. For example, when SNP1 through SNP78 are sequentially combined, a PID represented as AAAABB . . . BB may be generated.

FIG. 5 is a flowchart illustrating the operation of the secret key generating unit 12 included in the system of FIG. 1 according to an embodiment of the present invention. The operation of the secret key generating unit 12 will now be explained in detail with reference to FIGS. 1 and 5.

Referring to FIG. 5, in operation 510, the secret key generating unit 12 generates a PID by using genotypes of markers among the acquired genetic information. For example, the markers may be 78 markers, the genotypes of each of the markers may be represented as AA, BB, and AB, and the genotypes M, BB, and AB may respectively correspond to 0, 1, and 2. Reference numeral 511 denotes a PID generated from the genotypes of the 78 markers, and reference numeral 512 denotes 78 numbers corresponding to the genotypes of the markers.

In operation 520, the secret key generating unit 12 extracts a representative value from the generated PID. In detail, the PID consists of the 78 numbers 512, and a representative number is extracted from the 78 numbers 512. In this case, for example, the representative number may be extracted from the PID by using a hash function. Hashing is a method of converting one data stream into a relatively small number or key. Since an item can be faster searched by using the small number or key than by using the original data, the hashing can be used in indexing and searching for items in a database.

In operation 530, the secret key generating unit 12 corrects the extracted representative value according to an encryption algorithm. In detail, the secret key generating unit 12 may correct the extracted representative value to have a size suitable for the encryption algorithm. For example, when it is determined that the extracted representative value is not an 128-bit value suitable for the encryption algorithm, the secret key generating unit 12 corrects the extracted representative value to have 128 bits. Also, it is determined whether there is the same value as the extracted representative value in the samples. Although PIDs generated by using the genotypes of the markers according to the samples are different, the same representative value may be generated from the different PIDs.

In operation 540, the secret key generating unit 12 generates a secret key from the corrected representative value. Reference numeral 541 denotes a 128-bit secret key. Accordingly, the secret key is suitable for the encryption algorithm.

Figure 6A:
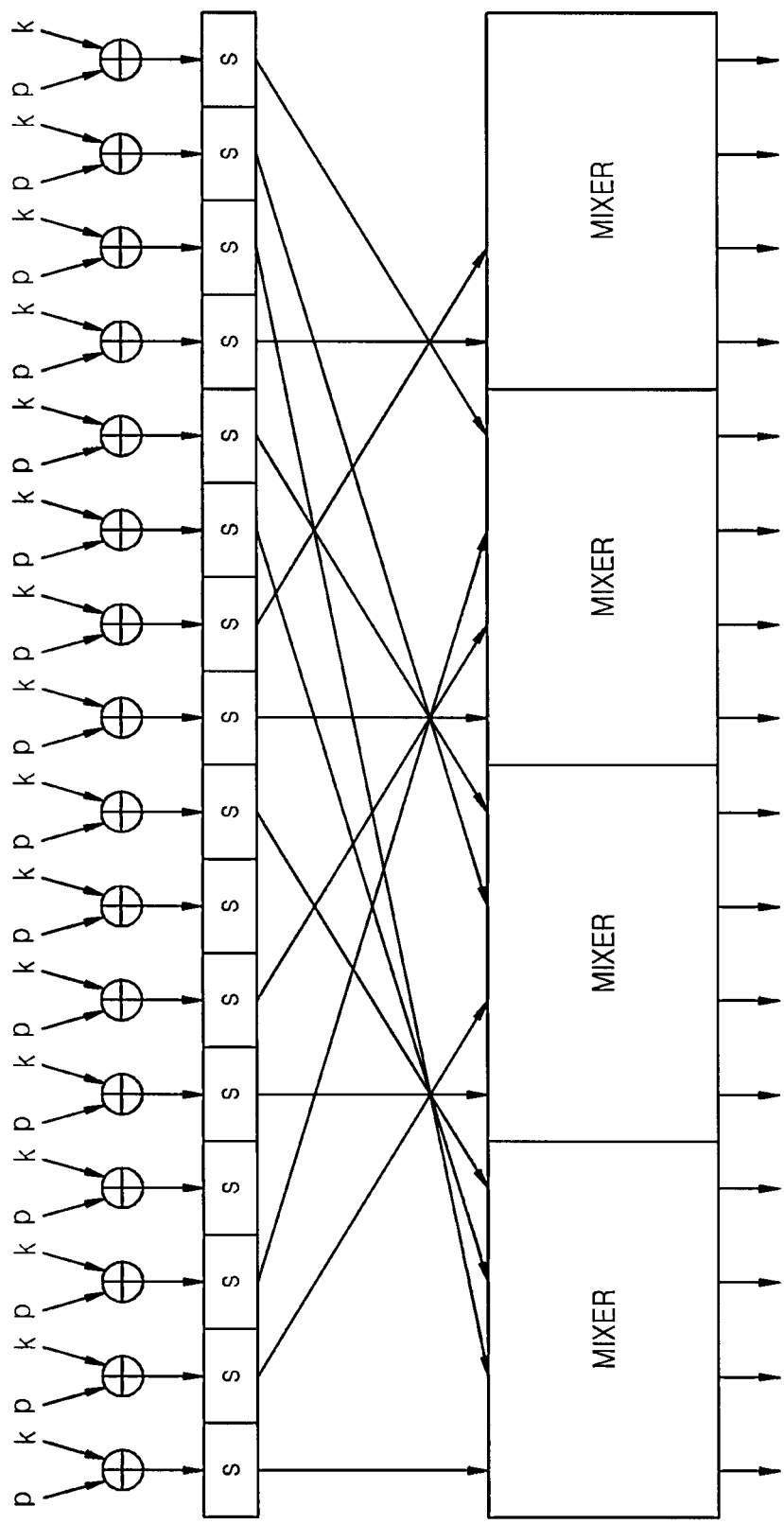
FIG. 6A is a block diagram of an encrypting unit included in the system of FIG. 1 according to an embodiment of the present invention.
Figure 6B:
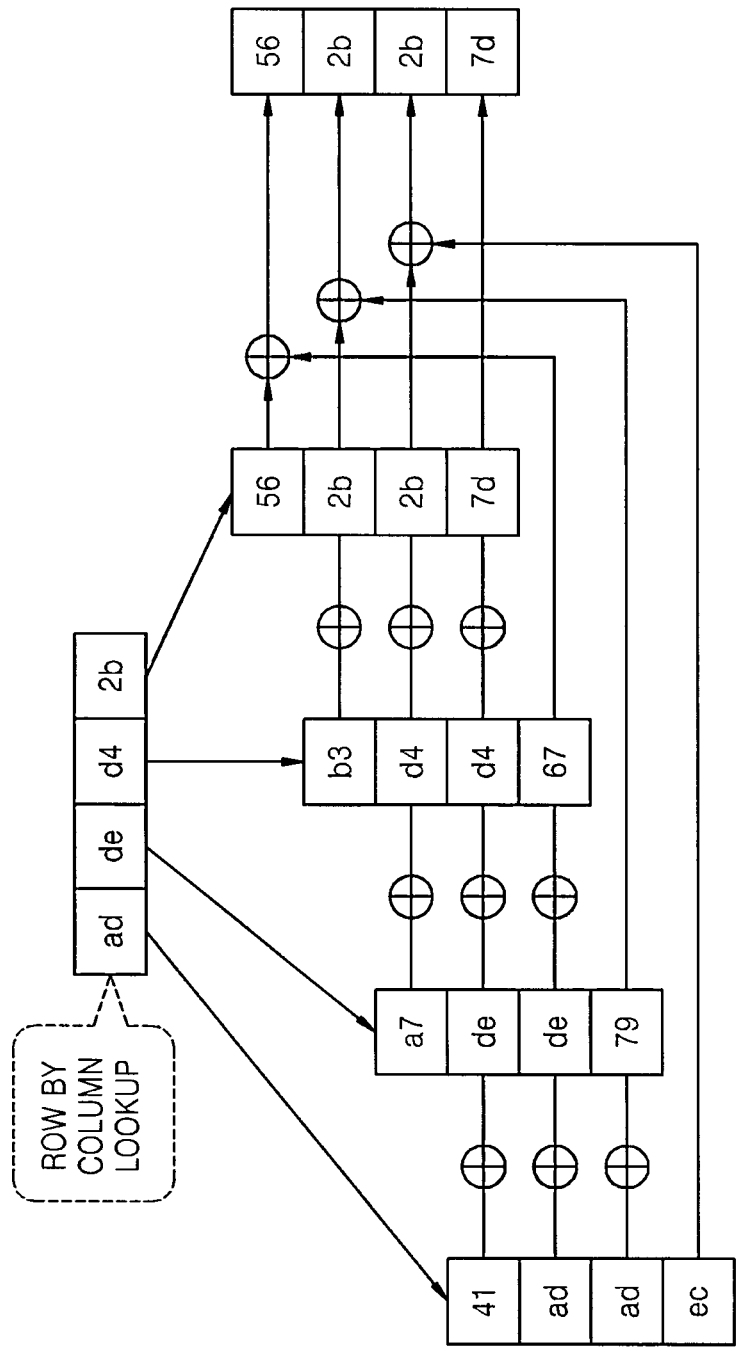
FIG. 6B illustrates an encryption algorithm applied to the encrypting unit included in the system of FIG. 1 according to an embodiment of the present invention.

FIG. 6A is a block diagram of the encrypting unit 13 included in the system of FIG. 1 according to an embodiment of the present invention. FIG. 6B illustrates an encryption algorithm applied to the encrypting unit 13 included in the system of FIG. 1 according to an embodiment of the present invention. The operation of the encrypting unit 13 will now be explained with reference to FIGS. 1, 6A, and 6B.

In FIG. 6A, 'p' denotes plaintext data, and may be the image data or numerical data output from the genetic information acquiring unit 11. 'k' denotes a key, and may be the secret key generated by the secret key generating unit 12.

The encrypting unit 13 may encrypt the acquired genetic information by using the secret key generated by the secret key generating unit 12. In detail, the encrypting unit 13 may encrypt the acquired genetic information by performing an encryption operation according to a symmetric key cryptography on the acquired genetic information and the generated secret key. The symmetric key encryption method may use a well-known symmetric key algorithm. For example, the symmetric key algorithm may be an American Encryption Standard (AES) algorithm. More information about the AES algorithm is disclosed in Federal Information Processing Standard Publication 197 (Nov. 26, 2001, NIST, USA).

As described above, the genetic information acquired by the genetic information acquiring unit 11 may be at least one of image data and numerical data. Accordingly, the encrypting unit 13 may encrypt the image data or numerical data by performing an encryption operation using a well-known symmetric key algorithm on the image data or the numerical data and the generated secret key.

Figures 7A, 7B:
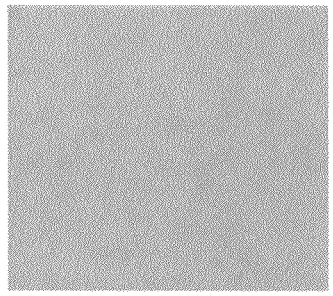
FIG. 7A illustrates encrypted image data output from the encrypting unit included in the system of FIG. 1.
FIG. 7B illustrates encrypted numerical data output from the encrypting unit included in the system of FIG. 1.

FIG. 7A illustrates encrypted image data output from the encrypting unit 13 included in the system of FIG. 1 according to an embodiment of the present invention. FIG. 7B illustrates encrypted numerical data output from the encrypting unit 13 included in the system of FIG. 1 according to an embodiment of the present invention.

Referring to FIGS. 7A and 7B, the image data of FIG. 7A is encrypted data generated by performing an encryption operation on the secret key generated by the secret key generating unit 12 and the image data of FIG. 2A. Accordingly, when the encrypted image data is transmitted, the genetic information of the person cannot be leaked without the person's consent, thereby preventing privacy invasion.

The numerical data of FIG. 7B is encrypted numerical data generated by performing an encryption operation on the secret key generated by the secret key generating unit 12 and the numerical data of FIG. 2B. Accordingly, when the encrypted numerical data is transmitted, the genetic information of the person cannot be leaked without the person's consent, thereby preventing privacy invasion.

Figure 8:
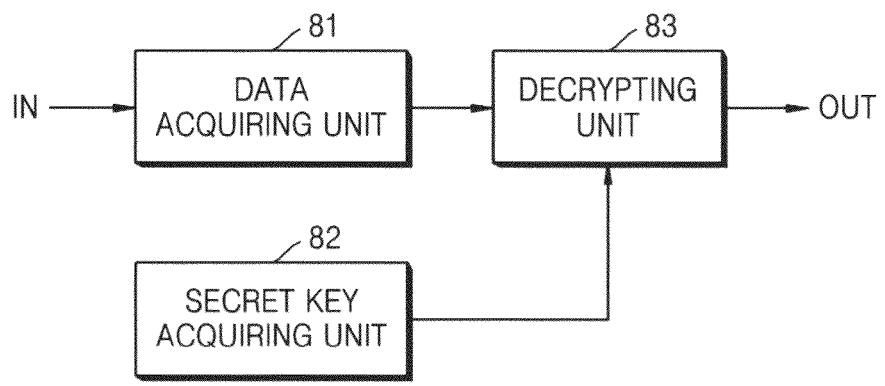
FIG. 8 is a block diagram of a system for decrypting information of a microarray according to an embodiment of the present invention.

FIG. 8 is a block diagram of a system for decrypting information of a microarray according to an embodiment of the present invention.

Referring to FIG. 8, the system may include a data acquiring unit 81, a secret key acquiring unit 82, and a decrypting unit 83.

The data acquiring unit 81 may acquire encrypted data corresponding to the information of the microarray. The encrypted data may be encrypted image data or encrypted numerical data.

The secret key acquiring unit 82 may acquire a secret key for identifying the unique property of a person from genetic information of the person. The operation of the secret key acquiring unit 82 will now be explained.

The secret key acquiring unit 82 may re-generate a secret key by performing an independent test on the basis of the genetic information of the person. For example, in decryption, the secret key acquiring unit 82 may collect a blood sample from the person, acquire genetic information from the collected blood sample, and re-generate a secret key on the basis of the acquired genetic information. In this case, a method of generating a secret key may be the same as the method of generating the secret key performed by the secret key generating unit 12 included in the system of FIG. 1. In other words, without storing a secret key used in encryption, a secret key may be re-generated in decryption and may be used in a decryption algorithm, thereby preventing the leakage of the genetic information of the person and protecting the person's privacy.

Alternatively, the secret key acquiring unit 82 may receive a secret key used in encrypting the information of the microarray. In this case, the secret key is distributed to a small number of specific participants, thereby preventing the leakage of the genetic information of the person as much as possible and protecting the person's privacy.

The decrypting unit 83 may decrypt the encrypted data by using the acquired secret key. In detail, the decrypting unit 83 may decrypt the encrypted data by performing a decryption operation according to a symmetric key cryptography on the encrypted data and the secret key acquired by the secret key acquiring unit 82. In other words, the decrypting unit 83 may perform decryption by using the decryption algorithm contrast to the encryption algorithm according to the cryptography of the genetic information of the microarray.

Figure 9:
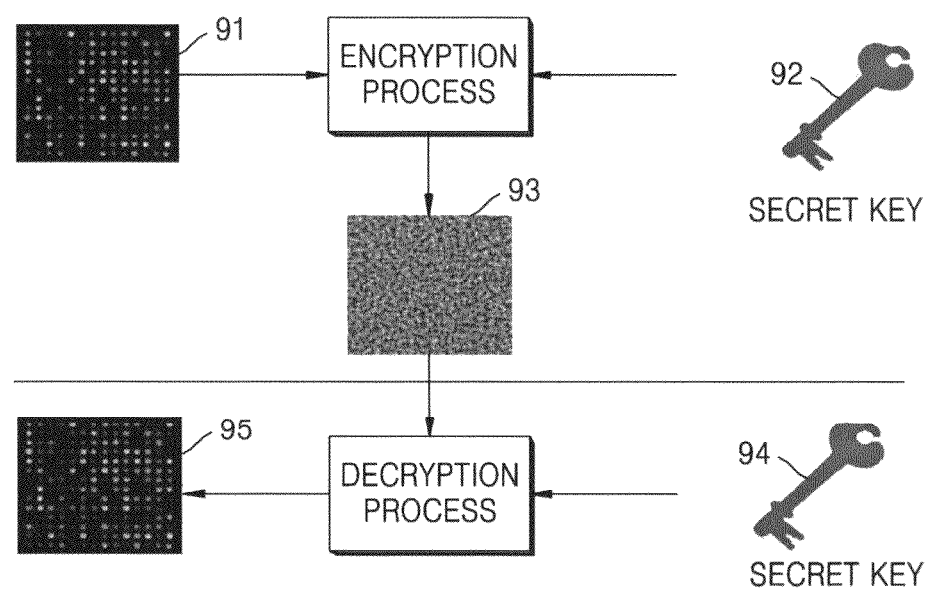
FIG. 9 illustrates encryption and decryption processes of information of a microarray according to an embodiment of the present invention.

FIG. 9 illustrates encryption and decryption processes of information 91 of a microarray according to an embodiment of the present invention.

Referring to FIG. 9, the information 91 of the microarray is encrypted by using a first secret key 92 to generate encrypted information 93. The information 91 of the microarray may be image data or numerical data. Since the first secret key 92, which is generated from genetic information of a person acquired from the microarray, is different for every individual, the unique property of the person can be identified by using the first secret key 92.

The encrypted information 93 is decrypted by using a second secret key 94, which is the same as the first secret key 92 used in the encryption process, to generate decrypted information 95. The second secret key 94 may be distributed by an independent test in the decryption process. Or, the first secret key 92 used in the encryption process may be received and used as the second secret key 94.

Accordingly, the encryption and decryption processes of FIG. 9 are based on a symmetric key or secret key cryptography. That is, a sender and a receiver of a message share a single secret key, the sender encrypts data by using the secret key, and the receiver receives and decrypts the encrypted data by using the secret key.

Figure 10:
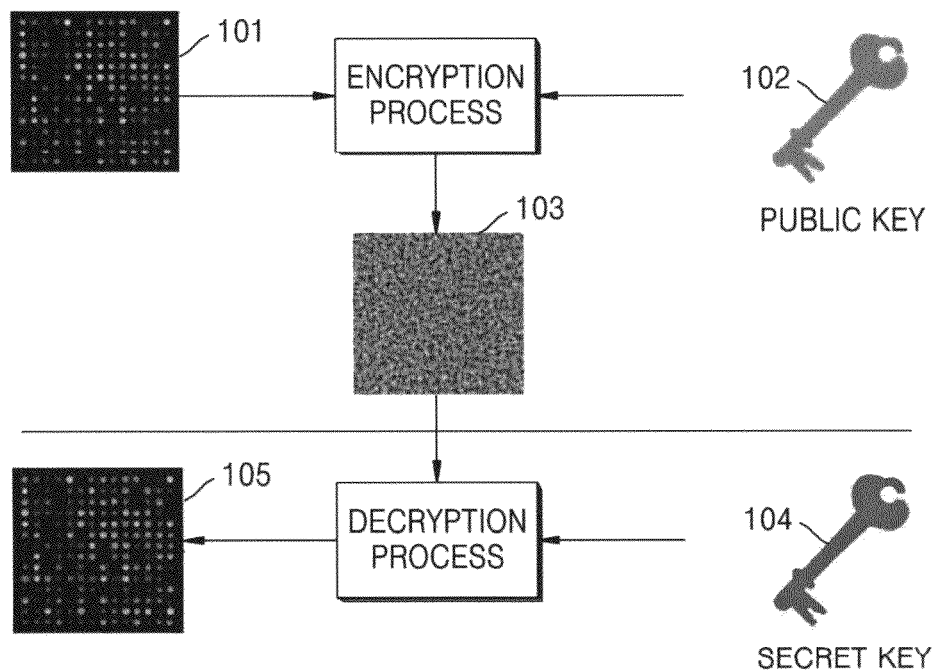
FIG. 10 illustrates encryption and decryption processes of information of a microarray according to another embodiment of the present invention.

FIG. 10 illustrates encryption and decryption processes of information 101 of a microarray according to another embodiment of the present invention.

Referring to FIG. 10, the information 101 of the microarray is encrypted by using a public key 102 to generate encrypted information 103. The information 101 of the microarray may be image data or numerical data.

The encrypted data 103 is decrypted by using a secret key 104, unlike in the encryption process, to generate decrypted information 105. The secret key 104 may be distributed by an independent test in the decryption process. Accordingly, the secret key 104, which is independently generated by using genetic information of a person and is different from the public key 102 used in an encryption algorithm, is used in a decryption algorithm, thereby preventing the encrypted data from being accessed by others.

Accordingly, the encryption and decryption processes of FIG. 10 are based on a public key cryptography. Among cryptographies for enhancing security, the public key cryptography is an asymmetric method in which different keys are used to encrypt and decrypt data. Since it is difficult to securely transmit and store a secret key, the public key cryptography is used to complement a secret key cryptography. Accordingly, the encryption and decryption processes of FIG. 10 can be applied to a public key cryptography.

Figure 11:
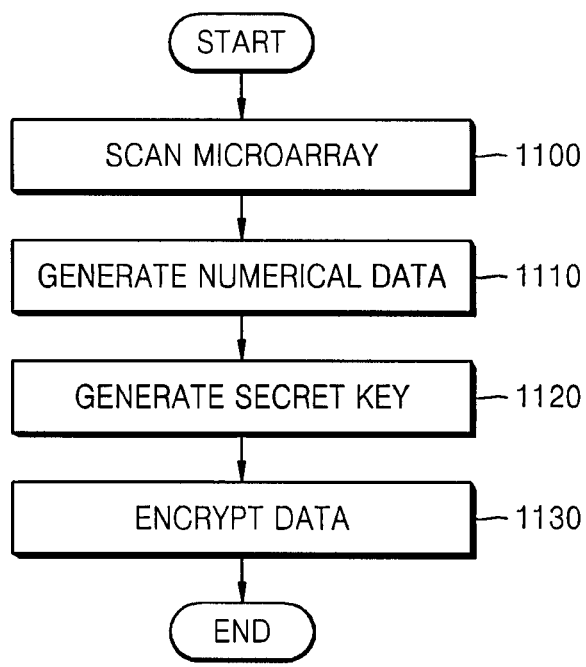
FIG. 11 is a flowchart illustrating a method of encrypting information of a microarray according to an embodiment of the present invention.

FIG. 11 is a flowchart illustrating a method of encrypting information of a microarray according to an embodiment of the present invention.

Referring to FIG. 11, the method includes operations sequentially performed by the system of FIG. 1. Accordingly, a repeated explanation of the same operations as those of the system of FIG. 1 will not be given.

In operation 1100, the genetic information acquiring unit 11 acquires image data by scanning the microarray.

In operation 1110, the genetic information acquiring unit 11 converts the acquired image data into numerical data.

In operation 1120, the secret key generating unit 12 generates a secret key for identifying the unique property of a person form the acquired genetic information.

In operation 1130, the encrypting unit 13 encrypts the image data or the numerical data by using the generated secret key.

In FIG. 11, operations 1100 through 1130 may be performed by a scanner. Accordingly, the encrypted image data or numerical data may be transmitted from the scanner through a communication network, such as the Internet, or portable storing media, such as CD, DVD, USB drivers thereby preventing the leakage of personal information.

Alternatively, operations 1100 and 1110 may be performed by a scanner, and operations 1120 and 1130 may be performed by a processing unit such as a computer. Accordingly, plaintext image data or plaintext numerical data output from the scanner may be transmitted through a communication network, such as the Internet, and may be received and encrypted by the processing unit such as the computer.

Figure 12:
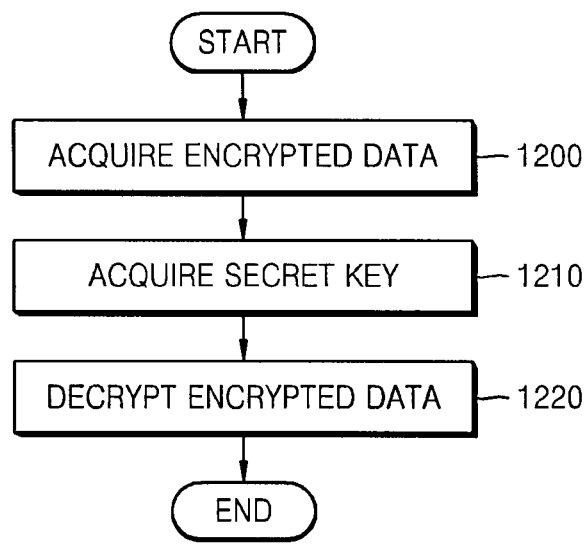
FIG. 12 is a flowchart illustrating a method of decrypting information of a microarray according to an embodiment of the present invention.

FIG. 12 is a flowchart illustrating a method of decrypting information of a microarray according to an embodiment of the present invention.

Referring to FIG. 12, the method includes operations sequentially performed by the system of FIG. 8. Accordingly, a repeated explanation of the same operations as those of the system of FIG. 8 will not be given.

In operation 1200, the data acquiring unit 81 acquires encrypted data corresponding to the information of the microarray. The encrypted data may be encrypted mage data or encrypted numerical data.

In operation 1210, the secret key acquiring unit 82 acquires a secret key for identifying the unique property of a person from genetic information of the person. As described above, the secret key acquiring unit 82 may re-generate a secret key by performing an independent test, or may receive a secret key used in encrypting the information of the microarray.

In operation 1220, the decrypting unit 83 decrypts the encrypted data by using the acquired secret key.

In addition to the above described embodiments, embodiments of the present invention can also be implemented through computer readable code/instructions in/on a medium, e.g., a computer readable medium, to control at least one processing element to implement any above described embodiment. The medium can correspond to any medium/media permitting the storing and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as carrier waves, as well as through the Internet, for example. Thus, the medium may further be a signal, such as a resultant signal or bitstream, according to embodiments of the present invention. The media may also be a distributed network, so that the computer readable code is stored/transferred and executed in a distributed fashion. Still further, as only an example, the processing element could include a processor or a computer processor, and processing elements may be distributed and/or included in a single device.

As described above, according to the above one or more embodiments of the present invention, since genetic information of a person is acquired by scanning the microarray, a secret key for identifying the unique property of the person is generated from the acquired genetic information, and the acquired genetic information is encrypted by using the generated secret key, the genetic information of the person can be prevented from being leaked and the person's privacy can be protected. In addition, since test results of the microarray can be publicized unless it invades personal information, test result transparency can be ensured and knowledge reproduction through shared information can be achieved.

While aspects of the present invention has been particularly shown and described with reference to differing embodiments thereof, it should be understood that these exemplary embodiments should be considered in a descriptive sense only and not for purposes of limitation. Any narrowing or broadening of functionality or capability of an aspect in one embodiment should not considered as a respective broadening or narrowing of similar features in a different embodiment, i.e., descriptions of features or aspects within each embodiment should typically be considered as available for other similar features or aspects in the remaining embodiments.

Thus, although a few embodiments have been shown and described, it would be appreciated by those skilled in the art that changes may be made in these embodiments without departing from the principles and spirit of the invention, the scope of which is defined in the claims and their equivalents.

What is claimed is:

1. A method of encrypting information of a microarray, the method comprising:
   acquiring genetic information of a person by scanning the microarray utilizing a genetic information acquiring unit;
   generating a personal identification (PID) by combining personal genotypes of one or more markers of the acquired genetic information utilizing a secret key generating unit;
   generating a secret key for identifying a unique property of the person based on the generated PID utilizing the secret key generating unit; and
   encrypting the acquired genetic information by using the generated secret key utilizing an encrypting unit.

2. The method of claim 1, wherein the acquiring of the genetic information comprises:
   acquiring image data by scanning the microarray; and
   acquiring numerical data from the acquired image data,
   wherein the generating of the secret key comprises generating the secret key from the image data or the numerical data,
   wherein the encrypting of the acquired genetic information comprises encrypting the image data or the numerical data by using the generated secret key.

3. The method of claim 1, further comprising adjusting a number of the one or more markers based on a number of probes analyzable from the microarray.

4. The method of claim 1, wherein the generating of the secret key from the generated PID comprises:
   generating a representative value extracted from the generated PID; and
   correcting the generated representative value to have a predetermined size suitable for an encryption operation of the genetic information,
   wherein the encrypting of the acquired genetic information comprises encrypting the acquired genetic information by using the corrected representative value.

5. The method of claim 4, wherein the generating of the secret key from the generated PID comprises determining whether the generated representative value is sufficient to identify the unique property of the person.

6. The method of claim 1, wherein the encrypting of the acquired genetic information comprises encrypting the acquired genetic information by performing an encryption operation according to a symmetric key cryptography on the acquired genetic information and the generated secret key.

7. A computer-readable medium having computer readable code to implement a method of encrypting information of a microarray, the method comprising:
   acquiring genetic information of a person by scanning the microarray utilizing a genetic information acquiring unit;
   generating a personal identification (PID) by combining personal genotypes of one or more markers of the acquired genetic information utilizing a secret key generating unit;
   generating a secret key for identifying a unique property of the person based on the generated PID utilizing the secret key generating unit; and
   encrypting the acquired genetic information by using the generated secret key utilizing an encrypting unit.

8. A method of decrypting information of a microarray, the method comprising:
   acquiring encrypted data corresponding to genetic information of the microarray utilizing a data acquiring unit;

acquiring a secret key for identifying a unique property of a person from genetic information of the person utilizing a secret key acquiring unit; and decrypting the encrypted data corresponding to genetic information of the microarray by using the acquired secret key utilizing a decrypting unit, wherein the secret key is generated based on a personal identification (PID) and the PID is generated by combining personal genotypes of one or more markers of the genetic information.

9. The method of claim 8, wherein the acquiring of the secret key comprises receiving a secret key used in an encryption process of the microarray.

10. The method of claim 8, wherein the decrypting of the encrypted data comprises decrypting the encrypted data by performing a decryption operation according to a symmetric key cryptography on the encrypted data and the acquired secret key.

11. A computer-readable non-transitory medium having computer readable code to implement a method of decrypting information of a microarray, the method comprising:

acquiring encrypted data corresponding to genetic information of the microarray utilizing a data acquiring unit;

acquiring a secret key for identifying a unique property of a person from genetic information of the person utilizing a secret key acquiring unit; and decrypting the encrypted data corresponding to genetic information of the microarray by using the acquired secret key utilizing a decrypting unit, wherein the secret key is generated by combining personal genotypes of one or more markers of the genetic information.

12. A system for encrypting information of a microarray, the System comprising:

a genetic information acquiring unit to acquire genetic information of a person by scanning the microarray;

a secret key generating unit configured to generate a personal identification (PID) by combining personal genotypes of one or more markers of the acquired genetic information;

the secret key generating unit further configured to generate a secret key for identifying a unique property of the person based on the generated PID; and an encrypting unit configured to encrypt the acquired genetic information by using the generated secret key.

13. The system of claim 12, wherein the genetic information acquiring unit acquires image data by scanning the microarray and acquires numerical data from the acquired image data, wherein the secret key generating unit generates the secret key from the image data or the numerical data, wherein the encrypting unit encrypts the image data or the numerical data by using the generated secret key.

14. The system of claim 12, wherein the secret key generating unit generates a representative value extracted from the generated PID and corrects the generated representative value to have a predetermined size suitable for an encryption operation of the genetic information, wherein the encrypting unit encrypts the r red genetic information by using the corrected representative value.

15. The system of claim 12, wherein the encrypting unit encrypts the acquired genetic information by performing an encryption operation according to a symmetric key cryptography on the acquired genetic information and the generated secret key.

16. A system for decrypting information of a microarray, the system comprising:

a data acquiring unit configured to acquire encrypted data corresponding to genetic information of the microarray;

a secret key acquiring unit configured to acquire a secret key for identifying a unique property of a person from genetic information; and a decrypting unit configured to decrypt the encrypted data corresponding to genetic information of the microarray by using the acquired secret key, wherein the secret key is generated based on a personal identification (PID) and the PID is generated by combining personal genotypes of one or more markers of the genetic information.

17. The system of claim 16, wherein the secret key acquiring unit receives a secret key used in an encryption process of the microarray.

* * * * *